US008575324B2

(12) United States Patent
Lal et al.

(10) Patent No.: US 8,575,324 B2
(45) Date of Patent: Nov. 5, 2013

(54) METHODS AND REAGENTS FOR MOLECULAR DETECTION OF HIV-1 GROUPS M, N AND O

(75) Inventors: Renu B. Lal, Atlanta, GA (US); Danuta Pieniazek, Suwanee, GA (US); Chunfu Yang, Tucker, GA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 1104 days.

(21) Appl. No.: 11/645,988

(22) Filed: Dec. 27, 2006

(65) Prior Publication Data

US 2007/0275372 A1    Nov. 29, 2007

Related U.S. Application Data

(63) Continuation of application No. 10/980,660, filed on Nov. 3, 2004, now abandoned, which is a continuation of application No. 09/890,551, filed as application No. PCT/US00/02498 on Feb. 1, 2000, now abandoned.

(60) Provisional application No. 60/118,357, filed on Feb. 3, 1999.

(51) Int. Cl.
*C07H 21/04* (2006.01)
*C12Q 1/04* (2006.01)
*C12Q 1/68* (2006.01)
*C12Q 1/70* (2006.01)

(52) U.S. Cl.
USPC ............ 536/24.33; 435/5; 435/6.1; 435/6.11; 435/6.12; 536/24.32

(58) Field of Classification Search
None
See application file for complete search history.

(56) References Cited

U.S. PATENT DOCUMENTS

| | | | |
|---|---|---|---|
| 5,599,662 A | 2/1997 | Respess | |
| 5,629,413 A | 5/1997 | Peterson et al. | |
| 5,786,177 A | 7/1998 | Moncany et al. | |
| 6,001,558 A | 12/1999 | Backus et al. | |
| 2003/0148280 A1* | 8/2003 | Harris et al. | 435/6 |
| 2003/0180759 A1 | 9/2003 | Delaporte et al. | |

FOREIGN PATENT DOCUMENTS

| | | |
|---|---|---|
| EP | 0293181 A | 11/1988 |
| EP | 0617132 A | 9/1994 |
| EP | 0887427 A | 12/1998 |
| FR | 2663040 A | 12/1991 |
| WO | WO 93/13223 A | 7/1993 |
| WO | WO 96/02557 A | 2/1996 |
| WO | WO 97/07808 A | 3/1997 |
| WO | WO 99/04011 * | 1/1999 |

OTHER PUBLICATIONS

Alberts et al, Simple, Sensitive, and Specific Detection of Human Immunodeficiency Virus Type 1 in Clinical Specimens by Polymerase Chain Reaction with Nested Primers, Journal of Clinical Microbiology, Jul. 1990, vol. 28, No. 7, p. 1560-1564.*
Abstract. "Human Immunodeficiency Virus Type 1 (HXB2), complete Genome" (1987).
Alaeus et al. "Subtype-specific problems with quantification of plasma HIV-1 RNA" AIDS 11(7):859-865 (Jun. 1997).
Cavert "In vivo detection and quantitation of HIV in blood and tissues" AIDS 12 (Suppl. A):S27-34 (1998).
Clewley et al. "A novel Simian Immunodeficiency Virus (SIVdrl) pol Sequence from Drill Monkey, *Mandrillus leucophaeus*" J. Virol. 72(12):10305-10309 (1998).
Eberle et al. "Diversity of the immunodominant epitope of gp41 of HIV-1 subtype O and its validity for antibody detection" J. Virol. Methods 67(1):85-91 (Aug. 1997).
Fransen et al. "Design and evaluation of new, highly sensitive and specific primers for polymerase chain reaction detecton of HIV-1 infected primary lymphocytes" Mol. Cell. Probes 8(4):317-322 (Aug. 1994).
Gao et al. "Orgin of HIV-1 in the Chimpanzee Pan troglodytes Troglodytes" *Nature* (London) 397(4):436-441 (1999).
Gao et al. "A comprehensive panel of near-full length clones and reference sequences for non-subtype B isolates of human immunodeficiency virus type 1" J. Virol. 72(7):5680-5698 (Jul. 1998).
Korber et al. "Human Retroviruses and AIDS 1998: A Compilation and Analysis of Nucleic Acid and Amino Acid Sequences" Online. Retrieved from the Internet: <URL:http://hiv-web.lanl.gov/> (2000).
Landegren et al. "DNA Diagnostics-Molecular Techniques and Automation" Science. 242(4876):229-237 (Oct. 14, 1988).
Loussert-Ajaka et al. "Variability of Human Immunodeficiency Virus Type 1 Group O Strains Isolated from Cameroonian Patients Living in France" J. Virol. 69(9):5640-5649 (Sep. 1995).
Loussert-Ajaka et al. "Genetic diversity and HIV detection by polymerase chain reaction" Lancet 346:1489 (Dec. 2, 1995).
NCBI HXB2 nucleotide sequence, gi8218025, Mar. 9, 1987.

(Continued)

*Primary Examiner* — Maria Marvich
(74) *Attorney, Agent, or Firm* — Klarquist Sparkman, LLP (57) ABSTRACT

Reagents and assays for detecting HIV-1 groups M and O and optionally HIV-1 group N and SIVcpz are provided. The reagents are nucleic acid primers for the hybridization to, amplification and subsequent detection of HIV-1 groups M, N and O and SIVcpz in a biological sample. The primers are oligonucleotides that selectively hybridize to the highly conserved regions of the env and pol regions of HIV-1. Due to the high sensitivity of the assays, small concentrations of HIV in a biological sample can be detected, allowing diagnosis at an early stage of infection. The assays are qualitative or quantitative and are useful for viral load determinations of HIV-1 groups M, N or O in a patient undergoing treatment for HIV-1 infection. Viral load determinations can be used to monitor the progress of the treatment regimen, the development of drug resistance, and to predict disease progression.

25 Claims, 2 Drawing Sheets

(56) References Cited

OTHER PUBLICATIONS

Owen et al. "Genetically Divergent Strains of Human Immunodeficiency Virus Type 2 Use Multiple Coreceptors for Viral Entry" J. Virol. 72(7):5425-5432 (Jul. 1998).

Pieniazek et al. "Phylogenetic Analysis of GP 41 Envelope of HIV-1 groups M,N, and O Strains provides an alternate region for subtype determination" Online (1998).

Respess et al. "Detection of genetically diverse human immunodeficiency virus type 1 group M and O isolates by PCR" J. Clin. Microbiol. 35(5):1284:1286 (May 1997).

Schreiber et al. "The risk of transfusion-transmitted viral infections. The Retrovirus Epidemiology Donor Study" New Engl. J. Med. 334(26):1685-1690 (Jun. 27, 1996).

Simon et al. "Identification of a New Human Immunodeficiency Virus Type 1 distinct from Group M and Group O" *Nature Medicine* 4(9):1032-1037 (1998).

Vanden Haesvelde et al. "Sequence Analysis of a Highly Divergent HIV-1 related Lentivirus isolated from a wild captured Chimpanzee" *Virology* 221(2):346-350 (1996).

Xiao et al. "CCR5 Coreceptor Usage of Non-Syncytium-Inducing Primary HIV-1 is Independent of Phylogenetically Distinct Global HIV-1 Isolates: Delineation of Consensus Motif in the V3 Domain That Predicts CCR-5 Usage" Virology 240(1):83-92 (Jan. 5, 1998).

Yang et al. "Detection of Phylogenetically diverse Human Immunodeficiency Virus Type 1 Groups M and O from Plasma by using Highly Sensitive and Specific Generic Primers" *J. Clin. Microbiol.* 8:2581-2586 (Aug. 1999).

\* cited by examiner

METHODS AND REAGENTS FOR MOLECULAR DETECTION OF HIV-1 GROUPS M, N AND O

This application is a continuation of U.S. application Ser. No. 10/980,660, filed on Nov. 3, 2004, now abandoned, which is a continuation of U.S. application Ser. No. 09/890,551 filed on Aug. 1, 2001, now abandoned, which is the National Stage of International Application No. PCT/U.S.00/02498, filed on Feb. 1, 2000, which claims the benefit under U.S.C. §119(e) of U.S. Provisional Application 60/118,357, filed on Feb. 3, 1999. U.S. application Ser. No. 10/980,660, filed on Nov. 3, 2004, U.S. application Ser. No. 09/890,551 filed on Aug. 1, 2001, International Application No. PCT/U.S.00/02498 filed on Feb. 1, 2000, and U.S. Provisional Application 60/118, 357, filed on Feb. 3, 1999 are hereby incorporated by reference in their entirety.

This invention was made at the Centers for Disease Control and Prevention. Therefore, the United States Government has certain rights in this invention.

FIELD OF THE INVENTION

The present invention relates to the fields of virology and molecular biology and provides methods and reagents for detecting human immunodeficiency virus (HIV) in a biological sample. More particularly, the methods detect the presence of HIV-1 envelope groups M, N and O by amplifying HIV-1 nucleic acid molecules in a biological sample using HIV-1 primers.

BACKGROUND OF THE INVENTION

One of the most ravaging diseases of the late twentieth century has been acquired immunodeficiency syndrome (AIDS), caused by infection with HIV. There are several known strains of HIV including HIV-1, a collective term referring to several strains isolated in Europe or America, and HIV-2, a strain endemic in many West African countries. HIV-1 is classified by phylogenetic analysis into three groups, group M (major), group O (outlier) and a new variant of HIV-1, designated group N, that has been identified with its epicenter in Cameroon (Simon et al., *Nat Med* 4:1032-1037 (1998)). All three HIV-1 groups cause AIDS.

Group M contains at least ten subtypes, referred to as A through J, based on the sequence heterogeneity of the envelope region. Group O includes most divergent viruses that do not cluster with group M strains. Group N includes viruses that are distinct from HIV-1 groups M and O. For example, detailed genetic analyses have placed the origin of the YBF30 virus of group N far from that of group O, somewhere between group M and simian immunodeficiency virus (SIV) cpz-gabs. The worldwide distribution of various group M HIV-1 subtypes is diverse, with subtype B being most prevalent in North America and Europe and subtype A being most prevalent in Africa. Whereas most subtypes are common in Central Africa, other areas have restricted distribution of genotypes; for instance subtype E is highly prevalent in Thailand, subtype C is common in India and South Africa, and subtype F is prevalent in Romania, Brazil and Argentina. Type O infections have been identified in the West Central African countries of Cameroon and neighboring countries, such as Equatorial Guinea and Gabon. The spread of group O infections to Europe and more recently to the United States has been documented, although all patients have had links to West Central Africa.

The wide divergence of the HIV-1 group O viruses has created serious public health concerns regarding the safety of the blood supply. Reports by Eberle et al., *J. Virol.* Methods 67:85-91 (1997), and Loussert-Ajaka et al., *J. Virol.* 69:5640-5649 (1995) have indicated that serologic screening assays based on group M viruses, such as HIV-1 subtype B-based assays, may be unable to consistently detect group O infected blood. The residual risk of HIV-transmission from transfusions of blood screened using current antibody and antigen tests is estimated by scientists such as Schreiber et al., *New Engl. J. of Med.* 334:1685 (1996), to be two blood donations per million in the United States. The prevalence of group O infections in Africa and the spread of type O infections to other continents emphasizes the need for improved screening of the international blood supply. Ideally, improved screening assays should be highly sensitive in detecting all variants of HIV-1 group M, N and O contamination in donor blood. In addition, the screening assays should be able to detect plasma viremia, thereby allowing for earlier detection of HIV-1 and reducing blood transfusion infections associated with "window period" cases in which an individual is infected with the virus, but has not yet produced detectable levels of antibody against the virus.

Most commercially available HIV diagnostic assays are based on the detection of anti-HIV antibodies and antigens. However, several reports have shown that antibodies against some variants of HIV-1 group O are not reliably detected by these assays, primarily due to diversity in the immunodominant regions of HIV-1. If undiagnosed, these HIV-infected individuals may engage in activities or conduct resulting in the spread of the virus. In addition, these undiagnosed individuals may remain untreated, allowing the disease to progress until the onset of immunodeficiency symptoms.

Some of the currently available HIV diagnostic tests and many of the viral load assay tests used to assess the success of therapeutic treatment are nucleic acid-based. (Respess et al., *J. Clin. Microbiol.* 35:1284-1286 (1997)). Scientists have reported that these nucleic acid-based assays exhibit reduced sensitivities for non-subtype B HIV isolates (Alaeus et al., *AIDS* 11:859-865 (1997)). Since therapeutic regimens are evaluated and monitored by analyzing viral loads, the inability of current assays to accurately quantitate the viral load of all subtypes is a detriment to successful therapy (Cavert, *AIDS* 12 (Suppl. A): S27 (1998)).

While several molecular detection assays have been described for the detection of proviral DNA from peripheral blood (Respess et al, *J. Clin. Micro.* 35:1284-1286 (1997); Fransen et al., Mol. Cellular Probes 8:317-322 (1994); Loussert-Ajaka et al., *Lancet* 346:912-913 (1995)), none can amplify both group M and O HIV-1 strains from plasma using a single assay.

Therefore, what are needed are methods for detecting group M, N and O HIV infections in blood plasma, serum or other biological samples using a single assay and methods for distinguishing between group M, N and O infections in biological samples. In addition, highly sensitive qualitative and quantitative assays for HIV-1 group M, N and O viruses are needed.

SUMMARY OF THE INVENTION

Highly sensitive methods and reagents for the molecular detection of group M, group N and group O nucleic acid molecules in biological samples are provided. The reagents include nucleic acid probes or primers that hybridize to group M, group N and group O HIV-1 nucleic acids and also include probes or primers that hybridize to SIV from chimpanzees (SIVcpz) that are closely related HIV-1 nucleic acids. The preferred nucleic acid probes and primers have the sequences set forth in SEQ ID NOS: 1-9. The methods employ the reagents to amplify and detect group M, group N and group O HIV-1 nucleic acid sequences and are useful for early diagnostic detection of group M, group N and group O infection in a patient. The methods and reagents can therefore be used to screen blood donors and donated blood for HIV contamination. The assay can also be modified for quantitative viral load determination of all HIV-1 strains. The methods and reagents are also useful for monitoring the success of particular antiviral therapies for patients receiving therapy and can be used to screen antiviral compounds for efficacy against HIV.

The methods described herein, also referred to herein as assays, employ a generic probe or a primer set based on a conserved immunodominant region of the HIV-1 transmembrane protein gp41 and a viral DNA integrating enzyme, integrase (IN). The assays are highly sensitive in detecting HIV-1 positive specimens of diverse geographic origin representing different subtypes of HIV-1 group M, as well as HIV-1 group O and the most recently discovered group N. In addition, the assays are useful for detecting viral RNA from HIV-1 seropositive specimens with plasma copy numbers below detection by commercially available viral load assays. The highly sensitive assays are useful for early detection of HIV-1, as well as viral load determination in clinical specimens from all HIV-1 infections regardless of genotypes and geographic origin. The generic probe or primer set is useful with known methods of quantitation of HIV-1 RNA in biological samples, such as plasma, for sensitive quantitation that is independent from genotype and geographic origin.

In accordance with the methods, a patient or donor sample is combined with one or more of the generic nucleic acid primers or probes described herein under hybridization conditions for selective hybridization of the probe or primer to HIV-1 nucleic acid molecules in the sample. The probes or primers hybridize to viral RNA or DNA present in the sample from both HIV-1 groups M and O. Additional probes or primers are included in the assay for the detection of group N HIV-1 and SIVcpz nucleic acids. Hybridization of the probes is detected by nucleic acid detection methods known to those skilled in the art. Hybridization of the primer set results in amplification of the HIV-1 RNA or DNA present in the sample using techniques such as reverse transcription (RT) and the polymerase chain reaction (PCR). The amplified viral nucleic acids (RNA and DNA) are then detected using known techniques.

The HIV-1 RNA/DNA detection methods are highly sensitive and, under optimal conditions, can be used to detect HIV-1 positive plasma and cell samples greater than 96% of the time. Additional sensitivity is achieved by subsequently employing additional amplification steps, such as amplification using a different gene region, to achieve as much as 100% detection of HIV-1 in an HIV-1 positive sample.

The use of the probes and primers in the assays described herein provide one or more of the following advantages. The assays provide highly sensitive as well as specific assays for diagnostic detection of HIV-1 group M, N and O viruses. The sequence analysis of amplified products permits phylogenetic clustering of HIV-1 strains. Use of the assays allows early detection of HIV-1 viremia during "window period" cases, and the methods can be adapted as quantitative viral load assays for detection of both group M and O, and optionally, group N HIV-1 strains.

BRIEF DESCRIPTION OF THE DRAWINGS

FIG. 2A depicts the relationships of sequences derived from the amplified integrase (IN) region, and 2B represents the gp41 region. The topology shows an overall branching order consistent with phylogenies previously reported for full length pol and env sequences. Trees were derived from nucleotide sequence alignments (consensus lengths of 183 bp and 348 bp, respectively) using the neighbor-joining method. Horizontal branch lengths are drawn to scale, with the bar indicating 0.10 nucleotide substitutions per site. Numbers at the nodes indicate the percentage of bootstrap values (out of 500) in which the cluster to the right is supported (only values equal or above 70% are shown). Brackets identify known HIV-1 (groups M, N and O) and SIVcpz (Pan troglodytes troglodytes and Pan troglodytes schweinfurthii) viral lineages.

DETAILED DESCRIPTION OF THE INVENTION

Reagents and methods for detecting both HIV-1 groups M and O, and optionally, HIV-1 group N and SIVcpz are provided. Kits containing the reagents for use in conducting the methods are also provided. The reagents are nucleic acid probes or primers for the replication, amplification and subsequent detection of HIV-1 groups M, N and O in a biological sample. The reagents also include nucleic acid probes or primers that hybridize to, and distinguish genetically diverse variants of SIV from chimpanzees that are closely related HIV nucleic acids, namely SIVcpzGAB, SIVcpzANT and SIVcpzUS. The assays and kits employ the probes for the direct detection of HIV-1 and employ the primers for HIV-1 nucleic acid amplification using amplification techniques such as RT and PCR. The assays are useful for diagnosing HIV-1 group M, HIV-1 group N, or HIV-1 group O infection in a patient. Due to the high sensitivity of the assays, small concentrations of HIV in a biological sample can be detected, which allows diagnosis at an early stage of infection. The assays are also useful for detecting HIV-1 contamination in a biological fluid such as blood. The assays are qualitative or quantitative and are therefore useful for viral load determinations of HIV-1 groups M, N or O in a patient undergoing treatment against HIV-1. Viral load determinations can be used to monitor the progress of the treatment regimen or the development of drug resistance and can be used to predict disease progression.

Definitions

The terms "a", "an" and "the" as used herein are defined to mean "one or more" and include the plural unless the context is inappropriate.

As used herein, the term "complementary DNA primer" means an oligonucleotide which anneals to an RNA molecule in a particular orientation to allow for the synthesis of a nascent DNA strand in the presence of the enzyme reverse transcriptase (RT) under the conditions described herein. Also as used herein, the "condition" or "conditions" under which a DNA strand is synthesized include the presence of nucleotides, cations and appropriate buffering agents in amounts and at temperatures such that the RNA molecule and the DNA primer will anneal and oligonucleotides will be incorporated into a synthesized DNA strand. The described conditions have been optimized from other known reverse transcriptase/complementary DNA (RT/cDNA) synthesis protocols. It is generally known that other conditions can be established for optimization of a particular RT reaction on the basis of protocols well known to one of ordinary skill in the art.

As used herein, the terms "primer pair" and "primer set" refers to two primers, one having a forward designation and the other having a reverse designation relative to their respective orientations on a double-stranded DNA molecule which consists of a sense and antisense sequence, such that under the amplification conditions described herein, the forward primer anneals to and primes amplification of the sense sequence and the reverse primer anneals to and primes amplification of the antisense sequence. Primers can be selected for use in the amplification reaction on the basis of having less than 50% G-C content, having minimal complementarity with other primers in the reaction (to minimize the formation of primer dimers) and having melting temperature (Tm) values with the range of reaction temperatures appropriate for the amplification method, preferably PCR. In addition, primers can be selected to anneal with specific regions of the RNA template such that the resulting DNA amplification product ranges in size from 100 to 500 base pairs in length and most preferably around 300 base pairs in length. For example, in the conditions described above, the primer pair can consist of the oligonucleotide of SEQ ID NO: 1 (GP40F1) as the forward primer and the oligonucleotide of SEQ ID NO:2 (GP41R1) as the reverse primer as describe in more detail below.

As used herein, the terms "detecting" or "detection" of the amplified DNA refers to qualitatively or quantitatively determining the presence of the amplified DNA strand. The amplification of the synthesized DNA or direct detection of viral DNA can be detected by any method for the detection of DNA known in the art. For example, detection of the amplified DNA can be by Southern blot hybridization assay, by visualization of DNA amplification products of specific molecular weight on ethidium bromide stained agarose gels, by measurement of the incorporation of radiolabeled nucleotides into the synthesized DNA strand by autoradiography or scintillation measurement, by ELISA modified for the capture of a detectable moiety bound to the amplified DNA, or any other detection method known to one of ordinary skill in the art. The preferred detection method is by hybridization of the amplified DNA to an internal specific oligoprobe using techniques such as ELISA, Southern blot hybridization or similar methods.

By "isolated" is meant nucleic acid free from at least some of the components with which it naturally occurs.

By "selective" or "selectively" is meant a sequence that does not hybridize with other nucleic acids to prevent adequate determination of an HIV-1 infection, depending upon the intended result. As used herein to describe nucleic acids, the term "selectively hybridizes" excludes the occasional randomly hybridizing nucleic acids, and thus has the same meaning as "specifically hybridizing".

By "probe" is meant a nucleic acid sequence that can be used for selective hybridization with complementary nucleic acid sequences for their detection. The probe can vary in length from about 5 to 100 nucleotides, preferably from about 10 to 50 nucleotides, most preferably about 25 nucleotides. The terms "probe" and "primer" are used interchangeably herein with the understanding that probes are used to directly or indirectly detect a nucleic acid whereas primers are used to amplify the nucleic acid and the amplified product is then detected. Generally, "probes" are labeled with a detectable label and "primers" are utilized in a set of two to hybridize to two different segments of a target nucleic acid molecule to amplify the sequence between those two segments.

As used herein, the term "highly conserved region" refers to those regions on a DNA or RNA molecule that are identical or nearly identical in related species or among various subspecies.

HIV-1 Group M, N and O Probes or Primers

The probes or primers used in the assays described herein are oligonucleotides, each having a nucleic acid sequence that specifically or selectively hybridizes under stringent hybridization conditions for selective hybridization to the complimentary, or opposite, strand of a highly conserved region of the nucleic acid molecule of the HIV-1 between nucleotide positions 7746 and 8459 of the HXB2 strain, for the env product, gp41, and between nucleotide positions 4596 and 5080 for the pol product, integrase. (GenBank Accession No. K03455). In a preferred embodiment, the probes or primers within this region selectively hybridize with all group M and O HIV-1 nucleic acids. In an alternative preferred embodiment, the probes or primers selectively hybridize with all group M, N and O HIV-1 nucleic acids and with chimpanzee SIV nucleic acids.

Preferably, the primers hybridize to a highly conserved region of the nucleic acid molecule encoding the env gene protein of the HIV-1 between the following nucleotide positions of the HXB2 strain: 7746 to 7772; 7817 to 7844; 8220 to 8258; and 8432 to 8459.

More preferably, the primers hybridize to a highly conserved region of the nucleic acid molecule encoding the gp41 protein of the HIV-1 between the following nucleotide positions of the HXB2 strain: 7789 to 7816; 8347 to 8374; 7850 to 7879; 8265 to 8294; and 8281 to 8310.

In an alternative preferred embodiment, the primers hybridize to a highly conserved region of the nucleic acid molecule encoding the integrase gene protein of HIV-1 between the following nucleotide positions of the HXB2 strain: 4596 to 4625; 5051 to 5080; 4724 to 4753; and 4956 to 4984.

Hybridization may be achieved under various temperatures and conditions, according to the temperature of dissociation (Td) of the molecules being hybridized and the stringency required for specific binding. The molecules can be hybridized to one another in any order or preferably at the same time. Reaction conditions for hybridization of an oligonucleotide, or polynucleotide, to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. Under extremely stringent hybridization conditions, only oligomers that are completely complementary to each other will remain hybridized to each other. In general, the longer the sequence or higher the G and C content, the higher the temperature required or salt concentration permitted. Chapter 11 of the well-known laboratory manual of Sambrook et al., MOLECULAR CLONING: A LABORATORY MANUAL, second edition, Cold Spring Harbor Laboratory Press, New York (1989), describes hybridization conditions for oligonucleotide probes and primers in great detail, including a description of the factors involved and the level of stringency necessary to guarantee hybridization with specificity. Hybridization techniques are well-documented in the scientific literature; one set of possible conditions is exemplified below.

Each primer is preferably a DNA molecule, most preferably a cDNA molecule, having a length of 18 to 40 nucleotides. More preferably, the length of the primer is 25 to 35 nucleotides. The most preferred primer length is 27 to 29 nucleotides. Depending on the length of the primer, the target hybridization region can range between 70% complementary bases and full complementarity and still hybridize under stringent conditions.

The selectively hybridizing nucleic acid primers described herein have at least 70%, 80%, 85%, 90%, 95%, 97%, 98%, and 99% complementarity with the segment of the sequence to which they hybridize. It will be understood that a combination of the probes and primers described herein can be combined to enable the detection of groups M, N and O HIV-1.

The primers are ideally used in primer pairs, containing a forward primer and a reverse primer, that hybridize to two different regions of HIV-1 nucleic acid molecule from groups M, N, and O within the highly conserved region of the env gene, particularly the small gp41 gene, or the pol gene, particularly the integrase genes. In the presence of reverse transcriptase, the HIV-1 nucleic acid sequence located between the hybridization regions is replicated and thereby amplified and subsequently detected. The length of the HIV-1 nucleic acid sequence being replicated is preferably 400 to 600 nucleotides. Nested primer pairs, in which a second primer pair hybridizes to and replicates a portion of the nucleic acid sequence replicated by a first primer pair, are useful for increasing amplification and thereby enhancing the specificity and sensitivity of an assay in which the primers are employed.

A preferred forward primer of a preferred primer pair for the detection of group M, N and O HIV-1 is the oligonucleotide of SEQ ID NO: 1 (GP40F1), which has the following nucleotide sequence, or conservative substitutions thereof:

5' TCTTAGGAGCAGCAGGAAGCACTATGGG 3'

A preferred reverse primer of the preferred primer pair for the detection of group M, N and O HIV-1 is the oligonucleotide of SEQ ID NO:2 (GP41R1), which has the following nucleotide sequence, or conservative substitutions thereof:

5' AACGACAAAGGTGAGTATCCCTGCCTAA 3'

For nested amplification for the detection of group M, N and O HIV-1, a preferred forward primer is the oligonucleotide of SEQ ID NO:3 (GP46F2), which has the following nucleotide sequence, or conservative substitutions thereof:

5' ACAATTATTGTCTGGTATAGTGCAACAGCA 3'

A preferred reverse primer for the detection of group M N and O HIV-1 for nested amplification is the oligonucleotide of SEQ ID NO:4: (GP47R2), which has the following nucleotide sequence:

5' TTAAACCTATCAAGCCTCCTACTATCATTA 3'

An alternate reverse primer for the detection of group N HIV-1 and SIVcpz is the oligonucleotide of SEQ ID NO:5 (GP48R2), which has the following nucleotide sequence, or conservative substitutions thereof:

5' TCCTACTATCTTAATGAATATTTTTATATA 3'

Another preferred forward primer of a preferred primer pair for the detection of group M, N and O HIV-1 is the oligonucleotide of SEQ ID No: 6 (INTF1), which has the following nucleotide sequence, or conservative substitutions thereof:

5' AGTGCTGCAGTTAAGGCAGCCTGTTGGTGG 3'

Another preferred reverse primer of the preferred primer pair for the detection of group M, N and O HIV-1 is the oligonucleotide of SEQ ID NO: 7 (INTR1), which has the following nucleotide sequence, or conservative substitutions thereof:

7 5' CTACCTGCCAGACAATCATCACCTGCCATC 3'

For nested amplification for the detection of group M, N and O HIV-1, another preferred forward primer is the oligonucleotide of SEQ ID NO: 8 (INTF2), which has the following nucleotide sequence, or conservative substitutions thereof:

5' AAGAGATCAAGCTGAACATCTTAAGACAGC 3'

Another preferred reverse primer for the detection of group M, N and O HIV-1 for nested amplification is the oligonucleotide of SEQ ID NO: 9 (INTR2), which has the following nucleotide sequence:

5' TGTATTACTACTGCCCCTTCACCTTTCCA 3'

It will be understood by those skilled in the art that oligonucleotides homologous to the primers described above will selectively hybridize, under hybridization conditions as described above, to the highly conserved region of the nucleic acid molecule encoding either the env gene protein, or to the pol gene protein of HIV-1, particularly the integrase protein. Preferably, the oligonucleotides have 90% or greater homology to the specific probe and primer sequences provided above and in the Sequence Listing. Homology is determined using a sequence/pattern computer program such as the BLAST™ 2.0 (gapped) sequence/pattern computer program or the CLUSTAL™ sequence alignment program using conditions and parameters well known to those skilled in the art. Therefore, these homologous primers are useful for the amplification and subsequent detection of HIV-1 nucleic acid molecules in a biological sample as described below and are therefore included within the scope of the present invention.

The probes and primers of SEQ ID NOS: 1-9 individually, in primer pairs, and in combination, (and those as modified by the above conditions) hybridize or anneal to all known HIV-1 group M, N SIV$_{op2}$, nucleic acid molecules and SIVcpz are therefore useful for the detection of these HIV-1 groups in biological samples obtained from various geographic locations throughout the world. In addition, the probes and primers are useful for both qualitative and quantitative detection of all known group M, N and O HIV-1 strains and may be useful for the detection of unknown group M, N and O HIV-1 strains. The ability of one or two sets of primers to detect such divergent subtypes of HIV-1 is highly unexpected, because, while the nucleotide region chosen for amplification is highly conserved, the same gp41 region shows considerable divergence between the immunodominant epitope of group M and O. Therefore, most serologic assays based on the detection of antibodies to the gp41 region prior to this discovery have been required to include a group O-specific peptide to enhance antibody detection as described by Loussert-Ajaka et al., *J. Virol.* 69:5640-5649 (1995) and Eberle et al., *J. Virol.* Methods 67:85-91 (1997).

It will be understood by those skilled in the art that the oligonucleotides described herein could be labeled with a detectable label, as described below, and used directly as HIV-1 group M and O nucleic acid detection probes in accordance with known methods.

Assay for Detecting HIV-1 Groups M, N and O

The probes and primers described above are useful in assays to detect, diagnose, quantify and monitor HIV-1 group M, N and O nucleic acids in a biological sample. In accordance with the method, one or more of the probes or primers, or one or more primer pairs, is combined with a biological sample to form an incubation mixture. The incubation mixture is reacted or incubated under conditions whereby the nucleic acid of the HIV-1 genome, including both RNA and DNA, and the primer will hybridize or anneal. An oligonucleotide strand is synthesized as an extension from the primer in the presence of a polymerase. The extension product is amplified using a second primer and suitable nucleic acid amplification reagents and conditions. The amplified product is then detected in accordance with methods known to those skilled in the art. Detection of the amplified nucleic acid indicates the presence of HIV-1 group M, N or O nucleic acids (DNA or RNA) in the biological sample.

The biological sample to be tested or analyzed may be taken from an individual, such as a wound, blood, secretion, tissue, bone, muscle, cartilage, or skin sample, or may be a laboratory research sample such as a cell culture supernatant, viral isolate or viral clones. The sample may be obtained from any biological source and is preferably taken from a human or animal, particularly a chimpanzee, capable of being infected with or harboring HIV-1. For example, the sample may be a biological fluid, such as whole blood, blood serum, blood plasma, urine, semen, saliva, sputum, cerebrospinal fluid, lacrimal fluid, lymph fluid, tissue culture fluid, ascites fluid, synovial fluid, pleural fluid, and the like. The preferred biological sample is a biological fluid from which cells can be removed or collected. The most preferred samples are blood plasma, serum and peripheral blood mononuclear cells isolated from entire blood.

The sample is collected or obtained using methods well known to those skilled in the art and may be diluted, purified, concentrated, filtered, dissolved, suspended or otherwise manipulated prior to use in the assay. Preferably, a sample containing particulate matter is diluted, filtered, or both diluted and filtered prior to use.

The preferred biological sample is a biological body fluid sample that is easily and routinely available, such as blood serum or plasma, saliva, cerebrospinal fluid and similar body fluids. The sample size for the biological fluid sample is preferably between approximately 0.25 μl and 1 ml.

For example, once the sample is obtained, viral RNA is extracted from the sample by methods known in the art, such as those taught by Sambrook et al., Molecular Cloning: A Laboratory Manual, 2nd ed. (Cold Spring Harbor Laboratory Press, New York, 1989), or from commercial kits, such as the QIAamp viral RNA extraction kit (Quiagen, Valencia, Calif.). The viral RNA is then used as a template to synthesize cDNA by using a polymerase, such as reverse transcriptase, or other replication methods known in the art.

The synthesized strand is amplified by any of the amplification protocols known in the art now or in the future, including but not limited to PCR, ligation amplification reaction (LAR), ligase-based amplification system (LAS), the self-sustained sequence replication (3SR) system, the transcription-based amplification system (TAS), and the Qβ replicase amplification method. The preferred amplification method is PCR.

For amplification by PCR, the conditions for amplification can include 30-40 cycles (preferably 35 cycles) of heating the synthesized DNA and primer pair at 93 to 97° C. (preferably 95° C.) for 30 to 90 seconds (preferably 30 seconds), at 45 to 57° C. (preferably 50-55° C.) for 30 to 90 seconds (preferably 30 seconds), and at 70 to 74° (preferably 72° C.) for 30 to 90 seconds (preferably one minute).

After amplification, or nested amplification, the amplified product is confirmed by methods known to those skilled in the art, such as electrophoresis, preferably using ethidium bromide staining and Southern blot hybridization methods. Alternatively, one or more of the nucleotides that are incorporated into the amplified product are labeled with a detectable label so that the amplified product itself is detectable. As a further alternative, the amplified product is detected by incubation with a detectable probe that selectively anneals to the amplified product and then detecting or measuring the concentration of the detectable probe. Detection of the detectable probe indicates the presence of HIV-1 RNA and/or DNA in the biological sample under investigation. If an HIV-1 group M, N or O RNA or DNA exists in the biological sample, the amplification product will be detected, preferably with a detection accuracy of greater than 96%. Additional sensitivity is achieved by subsequently employing additional amplification steps, such as amplification using other primers, particularly pol primers, to achieve as much as 100% detection of HIV-1 in an HIV-1 positive sample.

As described above, the assays particularly useful for the detection of group M, N and O RNA and/or DNA in a sample when the probes or primers for group M, N and O RNA or DNA (most preferably SEQ ID NOS: 1-4) are combined with the probes or primers specific for groups M, N and O and SIV SIVcpz RNA or DNA (most preferably SEQ ID NOS: 1-9).

Compositions and methods for labeling and detecting nucleotides or nucleic acid detection probes are well known to those skilled in the art. For example, the nucleotides or nucleotide triphosphates (NTPs) are labeled with biotin, which binds to streptavidin; digoxigenin, which binds to anti-digoxigenin; or 2,4-dinitrophenol (DNP), which binds to anti-DNP. The streptavidin or antibody molecule is conjugated to a detectable molecule, such as an enzyme that is then reacted with its substrate to produce a detectable reaction, such as a color change. Radioactivity, fluorogens, or chemiluminescent labels can also be used as labels. Examples of fluorogens include fluorescein and derivatives, phycoerythrin, allo-phycocyanin, phycocyanin, rhodamine, Texas Red or other proprietary fluorogens. The fluorogens are generally attached by chemical modification and bind to a fluorogenspecific antibody, such as anti-fluorescein. It will be understood by those skilled in the art that the nucleotides or probes can also be labeled by incorporation of a modified base containing any chemical group recognizable by specific antibodies. Other labels and methods of labeling nucleotides are well known to those skilled in the art. A review of nucleic acid labels can be found in the article by Landegren, et al., "DNA Diagnostics-Molecular Techniques and Automation", *Science*, 242:229-237 (1988). Most preferably, the nucleotide UTP is biotinylated.

If the biological sample is a patient sample, then the detection of HIV-1 nucleic acids in the sample using the oligonucleotide primers described herein indicates that the patient is infected with the virus. Therefore, the primers are useful in an assay for the diagnosis of HIV-1 infection.

Alternatively, if the biological sample is an individual blood sample or pooled blood sample from blood or a blood product that will be administered to a patient, such as a blood transfusion or blood clotting factor recipient, then the detection of HIV-1 nucleic acids in the sample using the oligonucleotide primers described herein indicates that the blood or blood product is contaminated with HIV-1 and should be discarded or treated to inactivate or remove the virus, thereby preventing transmission of the virus to the blood or blood product recipient. In addition, biological samples to be analyzed or processed by health care workers can be screened for HIV-1 contamination so that the individual handling the sample will exercise caution to prevent self-contamination and possible infection.

Use of the detection assay described herein will impact the safety of the blood supply by reducing blood transfusion associated HIV infections within the "window period." First, given the high sensitivity of detection, the assay will detect the presence of viral RNA early in the course of the infection. Second, testing of blood donations will not be dependent on the geographic origin of the donor. The very high sensitivity of the assay for any group M, N or O infection makes it an ideal candidate for genomic screening of the blood supplies maintained by all nations of the world.

In addition to being highly sensitive for detection of group M, group N and group O HIV-1, the assays are highly specific for HIV-1 and do not erroneously amplify or detect HIV-2 or SIV (other than chimpanzee) nucleic acid molecules. Further, the assay is highly accurate in that false positive results are minimized or entirely absent.

Viral Load Assay

Viral load determinations are commonly used to monitor the progression of HIV-1 infection and response to antiviral treatment in a patient who has been diagnosed as HIV-positive. An increase in viral load is an indication that the virus is not responsive to the therapy being administered, possibly indicating the onset of drug resistance. In addition, viral load determinations are used in laboratory research to assess HIV proliferation under certain conditions. For example, viral load determinations are made in the presence of an experimental antiviral therapy or drug to screen for new treatment regimens. Viral load determination may also be useful in determining the mechanisms of HIV replication so that additional therapies may be designed. These determinations provide a quantitative assessment of the concentration of virus in a sample.

The probes, primers and assays described above can be adapted for determining viral loads in a biological sample using the techniques of hybridization, replication, amplification and detection described above. The above-described assays are simultaneously conducted with assays using known or spiked quantities of virus in a control biological sample to produce a standard curve. By comparing the experimental assay results with the standard curve, the quantity of virus in the sample is determined. This quantity is defined mathematically as the viral load.

The measurement of plasma HIV-1 RNA has become an important tool in the clinical management of HIV-1 infected persons, and has clear advantages over other virological assays. In contrast HIV-1 p24 antigen levels, plasma viremia is measurable in a vast majority of HIV-infected patients at various stages of disease. In contrast HIV-1 proviral DNA levels in peripheral mononuclear cells, HIV-1 RNA levels in plasma change dynamically in response to successful therapy. Therefore, HIV-1 RNA levels in plasma are the most effective single predictor of clinical outcome. However, a disadvantage of currently available commercial viral load assays is that they are unable to detect certain group M non-B subtypes and many group O viruses. In contrast, the group M, N and O primers described herein allow amplification of all subtypes of group M as well as group O viruses. Thus, currently available assays, such as the AMPLICOR™, Nuclisense™ and Quantiplex™ nucleic acid amplification methods, can be adapted, by use of the primers described herein, to accurately quantitate virtually any HIV-1 RNA or DNA targets from any specimen regardless of geographic origin or viral genotype, and thereby provide a rapid, efficient and accurate test for monitoring response to therapy.

HIV-1 Detection Kits

Kits for detecting HIV-1 groups M, N and O virus in a biological sample contain one or more of the oligonucleotide probes or primers described herein and reagents for the detection of viral RNA or DNA to which the probes or primers have hybridized, either by detection of a hybridized probe or detection of an amplified product. The probes, primers and reagents are provided in separate containers or are combined in a single container depending on the assay employed and the stability of the components when combined.

The kit may optionally contain additional primers, such as primers composing a nested primer pair, a hybridization probe for detection of the amplified DNA product, an apparatus for conducting the assay, an apparatus for assay detection, one or more containers for obtaining and storing the sample prior to and during analysis, and suitable buffers, cations, nucleotides and other reagents to facilitate nucleic acid isolation, extraction, hybridization, synthesis, amplification and detection. In addition, the kit may contain reagents for confirming amplification, such as ethidium bromide, and reagents for the preparation of a standard curve, such as known concentrations or aliquots of the target nucleic acid molecule to be amplified by the primers.

The kits may also contain probes or primers specific for the detection or amplification of group N HIV-1. Alternatively, separate kits may be available for group N detection.

The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLE 1

Determination of HIV-1 Assay Sensitivity and Specificity

Blood plasma samples obtained from HIV-positive patients were tested using gp41 HIV-1 primers (SEQ ID NOS:1-5) to amplify and detect HIV-1 nucleic acids.

Primers for Detection of HIV-1 Groups M and 0

The following oligonucleotides, referred to herein as consensus primers or gp41 primers, were synthesized at the Biotechnology Core Facility, Centers for Diseases Control and Prevention (Atlanta, Ga.).

```
For reverse transcription and primary PCR, the
following primers were used:
GP40F1 (forward)
                                              (SEQ ID NO:1)
5' TCTTAGGAGCAGCAGGAAGCACTATGGG GP41R1 (reverse)
                                              (SEQ ID NO:2)
5' AACGACAAAGGTGAGTATCCCTGCCTAA For nested PCR, the following primers were used:
GP46F2 (forward)
                                              (SEQ ID NO:3)
5' ACAATTATTGTCTGGTATAGTGCAACAGCA GP47R2 (reverse)
                                              (SEQ ID NO:4)
5' TTAAACCTATCAAGCCTCCTACTATCATTA GP48R2 (reverse)
                                              (SEQ ID NO:5)
5' TCCTACTATCTTAATGAATATTTTTATATA 3'
```

The sensitivity of the assay for HIV-1 group M specimens (viral isolates) was examined using viral DNA. Viral isolates representing various group O and group N HIV-1 subtypes, HIV-2 isolates and SIV isolates were expanded as described by Xiao et al., *Virol.* 240:83-92 (1998) and Owen et al., *J. Virol.* 72:5425-5432 (1998). The SIV isolates were either obtained from the AIDS Reagent and Reference Program (Rockville, Md.) or were primary isolates obtained from naturally infected monkeys. Viral RNA was extracted from the culture supernatants and tested for initial sensitivity and specificity of the primers.

Full-length cloned sequences of HIV-1 subtype A-H (Gao et al., *J. Virol.* 72:5680-5688 (1998)) were employed to determine the sensitivity of the primers. Serial dilutions with known copy numbers of full length genomic clones representing subtypes A (92UG037.1), B (YU2, SG3), C (92BR025.8), D (94UG114.1), A/E (90CF402.8), F (93BR020.1), A/G (92NG003.1) and H (90CF056.1) demonstrated that most subtypes were detectable in an agarose gel assay at one to five copies/PCR reaction. Thus, the gp41 group M and 0 primer set (GP46F2 and GP47R2, referred to herein as gp46/47) as well as the group M, N, O and SIVcpz primer set (GP46F2 and GP48R2, referred to herein as gp46/48) were highly sensitive for detection of viral DNA regardless of viral genotypes.

Further analysis also revealed that the primers (gp46/47) were specific for HIV-1 only, since the culture supernatants from primary HIV-2 isolates (GB87, IC77618, IC310319, IC310072, SLRHC14), SIV isolates (MAC239, SMM 1, SIV-ST, M156, SM55, SM74) and an SIV chimpanzee isolate (SIVcpz) could not be amplified by gp46/47. However, the gp46/48 primers amplify three of the four known chimpanzee viruses known to date.

The results are shown below in Table 1.

TABLE 1

Sensitivity of gp46/47 and gp46/48 primers in detecting HIV-1 clones and proviral DNAs of HIV-1 Groups M, 0, and N and SIVcpz Group Group M/N/0/ Copies/ M/0 SIVcpz

| HIV/SIV groups | Copies/ PCR | Group M/O gp46/47 | Group M/N/O/SIVcpz gp46/48 |
|---|---|---|---|
| Group M | | | |
| Subtype A | | | |
| 92UG037.1 | 5 | + | + |
| | 1 | + | + |
| Subtype B | | | |
| YU2 | 5 | + | + |
| | 1 | − | − |
| SG3 | 5 | + | + |
| | 1 | + | + |
| Subtype C | | | |
| 92BR025.8 | 5 | + | + |
| | 1 | + | + |
| Subtype D | | | |
| 94UG114.1 | 5 | + | + |
| | 1 | + | + |
| Subtype A/E | | | 90CF402.8 |
| | 5 | + | + |
| | 1 | − | − |
| Subtype F | | | |
| 93BR020.1 | 5 | + | + |
| | 1 | − | − |
| Subtype A/G | | | |
| 92NG003.1 | 5 | − | − |
| | 1 | + | + |
| Subtype H | | | |
| 90CF056.1 | 5 | + | + |
| | 1 | + | + |
| Group O | | | |
| 11516(MD) | | + | + |
| 191265(CA) | | + | + |
| Group N | | | |
| YBF3O | | + | + |
| SIVcpz | | | |
| SIVcpzUS | | + | + |
| SIVcpzGAB1 | | − | + |
| SIVcpzGAB2 | | − | − |
| SIVcpzANT | | − | + |

EXAMPLE 2

Detection of HIV-1 Group M and 0 RNA in International HIV-Positive Samples

Blood plasma samples obtained from various HIV-positive patients were tested using the gp41 HIV-1 primers to amplify and detect HIV-1 nucleic acids as described in Example 1 above.

Sample Selection and RNA Extraction

Plasma samples to be tested using the primers described above were obtained from various ongoing HIV studies around the world. All samples had previously been shown to have antibodies HIV-1. These included serum and/or plasma specimens from Uganda (n=54), Thailand (n=43), Cameroon (n=40), Ivory Coast (n=29), Argentina (n=27), Brazil (n=23), United States (n=16), Ghana (n=8), Mexico (n=8), China (n=6), Lebanon (n=5), Zimbabwe (n=4), S. Africa (n=4), Spain (n=4), India (n=3), and miscellaneous (n=7). The specificity of the assay was tested against specimens from HIV-2 infected individuals from the Ivory Coast (n=19) and Ghana (n=2), as well as HIV seronegative donors from the United States (n=41). HIV-1 early seroconversion panels (five panels) were obtained from Boston Biomedica Inc. (Boston, Mass.).

Plasma viral RNA was extracted from each sample using a QIAamp™ viral RNA extraction kit according to the manufacturer's protocol (Quiagen, Valencia, Calif.). 200 μL of plasma were mixed with 800 μL of lysis buffer AVL. After a 10 minute incubation at room temperature, 800 μL of 100% ethanol was added to the lysate. The mixture was filtered through a column by centrifugation. After washing with buffer AW, the RNA was eluted from the column by adding 50 μL of RNAse-free water. For negative controls, normal human plasma RNA was extracted simultaneously.

Reverse Transcription, PCR and Nested PCR

Viral RNA (3-10 μL) from each sample was used to synthesize cDNA using 20 μM of the primer GP41R1 (SEQ ID NO:2) and a GeneAmp.™. RNA PCR kit with 5 mM MgCl.sub.2 following the manufacturer's protocol (Perkin-Elmer Cetus, Norwalk, Conn.).

The 20 μL cDNA reaction was added to a PCR mixture containing 50 μM of GP40 μl (SEQ ID NO: 1) and 30 μM of GP41R1 (SEQ ID NO:2), 1× GeneAmp.™. PCR buffer II (Perkin-Elmer Cetus, Norwalk, Conn.), 1-25 mM MgCl.sub.2, 2.5 U of AmpliTaq.™. DNA polymerase (Perkin-Elmer Cetus, Norwalk, Conn.), and the mixture was brought to a final volume of 100 μL with sterile distilled water. After initial denaturation at 94.degree. C. for two minutes, 35 cycles of PCR were performed in the GeneAmp.™. 9600 nucleic acid amplifier (Perkin-Elmer Cetus, Norwalk, Conn.). Each cycle consisted of denaturation at 94.degree. C. for 30 seconds, annealing at 50.degree. C. for 30 seconds, and extension at 72.degree. C. for 60 seconds, with a final extension at 72.degree. C. for five minutes. For nested PCR, 5 μL of the primary PCR product was added to a 100 μL PCR reaction mixture containing the same reagents as primary PCR except that the primers were replaced by 25 pM of each GP46F2 (SEQ ID NO:3) and GP47R2 (SEQ ID NO:4). The PCR reactions were subjected to 35 cycles using the same conditions as the primary PCR.

After PCR, the nested PCR products of expected size (460 bp) were detected by electrophoresis in 1.5% agarose gels along with a 100 bp ladder (Gibco, Grand Island, N.Y.) and visualized under ultraviolet light (UV) by ethidium bromide staining. Sequence analysis confirmed gp41 regions. The same procedure also successfully amplified and detected viral DNA extracted from patient peripheral blood mononuclear cells (PBMCs).

EXAMPLE 3

Determination of gp41 Amplification Assay Sensitivity in Clinical Specimens Including Group M and Group O The sensitivity of plasma RNA detection using the gp41 assay, as described in Example 1, was examined using a panel of plasma for which viral subtypes were already established by phylogenetic analysis of the envelope region (C2V3 or gp41).

RT-PCR analysis of 68 specimens having HIV-1 subtype A infections, obtained from diverse geographic locations, revealed that the nucleic acid molecules from 67 of the specimens (98.5%) could be amplified using the gp41 amplification assay, as shown in Table 2 below.

TABLE 2

Detection of plasma RNA from phylogenetically distinct HIV-1 group M and group O specimens using generic primers gp46/47

| HIV type | Country of origin | Number tested | Number positive | % positive |
|---|---|---|---|---|
| 1. Group M: Subtype A | | | | |
| | Ivory Coast | 20 | 19 | 95 |
| | Uganda | 24* | 24 | 100 |
| | Cameroon | 15 | 15 | 100 |
| | Ghana/Lebanon | 6/3 | 9 | 100 |
| | Total | 68 | 67 | 98.5 |
| | United States | 11 | 11 | 100 |
| | Mexico | 8 | 8 | 100 |
| | Brazil | 19 | 17 | 90 |
| | China | 6 | 6 | 100 |
| | Thailand | 20 | 20 | 100 |
| | Misc. | 7 | 7 | 100 |
| | Total | 71 | 69 | 97.2 |
| Subtype C | | | | |
| | Zimbabwe | 4 | 4 | 100 |
| | S. Africa | 4* | 4 | 100 |
| | India | 3 | 3 | 100 |
| | Uganda | 4 | 4 | 100 |
| | United States | 3 | 3 | 100 |
| | Lebanon | 1 | 1 | 100 |
| | Total | 19 | 19 | 100 |
| Subtype D | | | | |
| | Uganda | 26 | 26 | 100 |
| | Lebanon | 1 | 1 | 100 |
| | Total | 27 | 27 | 100 |
| Subtype E | | | | |
| | Thailand | 23 | 23 | 100 |
| Subtype F | | | | |
| | Argentina | 27* | 27 | 100 |
| | Brazil | 4 | 4 | 100 |
| | Japan | 2 | 2 | 100 |
| | Total | 33 | 33 | 100 |
| Subtype G | | | | |
| | Ghana/Lebanon | 2/1 | 3 | 100 |
| | Ivory Coast | 9 | 9 | 100 |
| | Total | 12 | 12 | 100 |
| 2. Group O | | | | |
| | Cameroon | 25 | 25 | 100 |
| | Spain | 5 | 5 | 100 |
| | United States | 2 | 2 | 100 |
| | Total | 32 | 32 | 100 |
| 3. HIV-2 | | | | |
| | Ivory Coast | 19 | 0** | 0 |
| | Ghana | 2 | 0 | 0 |
| | Total | 21 | 0 | 0 |
| 4. HIV negative | | | | |
| | United States | 41 | 0 | 0 |

*Represents one specimen each of potential recombinant with discordance in env and prt subtype: specimen from Uganda represents A env/B-Dprt, specimen from South Africa is C env/Bprt, and specimen from Argentina is F env/Bprt.
**Three specimens include persons with HIV-1 and HIV-2 dual infections.

Likewise, 69 of 71 (97%) subtype B, 19 of 19 (100%) subtype C, 27 of 27 (100%) subtype D, 23 of 23 (100%) subtype E, 33 of 33 (100%) of subtype F, and 12 of 12 (100%) subtype G gave a positive reaction using the gp41 amplification assay. Overall sensitivity of the gp41 amplification assay for plasma detection of HIV-1 group M subtypes was 98.8% (250 of 253). The three specimens testing negative by the GP46F2 (SEQ ID NO:3) and GP47R2 (SEQ ID NO:4) primer set were amplified using the GP46F2 and GP48R2 (SEQ ID NO:5) primer set, suggesting that the sequence variation on the GP47R2 primer may be the reason for lack of gp41 amplification.

The gp41 amplification assay was also able to amplify plasma viral RNA from individuals infected with HIV-1 group O viruses. Of the 32 group O plasma representing specimens from Cameroon, Spain, Belgium and US, 32 (100%) were amplifiable with the gp41 amplification assay.

The gp41 amplification assay is highly specific for HIV-1 only, because neither plasma from HIV-2 (n=21) nor uninfected controls (n=41) were amplified in the assay as shown in Table 2. The three specimens that tested positive using the gp41 group M and O primers in the HIV-2 infected group were from persons dually infected with HIV-1 and HIV-2.

Additional testing of gp41 (46/48) was performed using RNA from clinical specimens. The results are shown in Table 3 below.

TABLE 3

Detection of plasma RNA from phylogenetically distinct HIV-1 group M, N, and O specimens using generic primers gp46/48 1

| | | | | |
|---|---|---|---|---|
| 1. Group M: | | | | |
| Subtype A | | | | |
| | Ghana | 14 | 14 | 100 |
| | Ivory Coast | 26 | 16 | 100 |
| | Uganda | 20 | 20 | 100 |
| | Misc. | 4 | 4 | 100 |
| | Total | 64 | 64 | 100 |
| Subtype B | | | | |
| | Brazil | 19 | 19 | 100 |
| | Thailand | 20 | 20 | 100 |
| | Misc. | 16 | 15 | 93.8 |
| | Total | 55 | 54 | 98.2 |
| Subtype C | | | | |
| | Uganda | 5 | 5 | 100 |
| | Zimbabwe | 13 | 13 | 100 |
| | Misc. | 3 | 3 | 100 |
| | Total | 21 | 21 | 100 |
| Subtype D | | | | |
| | Uganda | 31 | 31 | 100 |
| | Lebanon | 1 | 1 | 100 |
| | Total | 32 | 32 | 100 |
| Subtype L | | | | |
| | Thailand | 23 | 23 | 100 |
| Subtype F | | | | |
| | Argentina | 26 | 25 | 96.2 |
| | Brazil | 4 | 4 | 100 |
| | Japan | 2 | 2 | 100 |
| | Total | 32 | 31 | 96.9 |
| Subtype G | | | | |
| | Ivory Coast | 10 | 9 | 90 |
| | Ghana | 5 | 5 | 100 |
| | Lebanon | 1 | 1 | 100 |
| | Total | 16 | 15 | 93.8 |
| 2. Group O | | | | |
| | Cameroon | 26 | 26 | 100 |
| | Spain | 5 | 5 | 100 |
| | United States | 2 | 2 | 100 |
| | Total | 32 | 32 | 100 |
| 3. Group N | Cameroon (DNA) | 1 | 1 | 100 |
| 4. HIV-negative | | 41 | 0 | 0 |

EXAMPLE 4

Determination of HIV-1 Assay Sensitivity for Group M, Subtype B

Assay Detection Sensitivity

HIV-1 stock at 1000, 100, 50, 25, 10 and 1 copies/ml was spiked in normal human plasma to test the sensitivity of detection using the primer sets and methods of the gp41 HIV-1 amplification assay described in Example 1. Ten microliters of viral RNA in duplicate from each sample was used to synthesize cDNA. The total cDNA reaction was then used for primary PCR. Following primary PCR, 5 μL of the primary PCR product were used for the nested PCR. Amplification was confirmed by electrophoresis and ethidium bromide staining.

In vitro spiking of HIV-1 subtype B with known copies in the plasma prior to RNA extraction and RT-PCR established that the gp41 group M and O primers were able to reliably detect as few as 25 copies/ml of HIV-1 RNA in an agarose gel assay.

The sensitivity of the assay for early detection of plasma viremia in seroconversion cases was examined. Analysis of five seroconverters from the United States (all subtype B) revealed that in all cases, RT-PCR detection preceded both HIV-1 antibody and p24 antigen detection. The early detection levels were comparable to other RNA based detection assays. However, in one case the gp41 group M, N and O assay was more sensitive for early detection of plasma viremia during the "window period." The gp46/48 primers gave the same results as the gp46/47 primers.

EXAMPLE 5

Comparison of gp41 HIV-1 Amplification Assay with Commercially Available Viral Load Assays The assay described above in Example 1, referred to herein as the gp41 assay, was used to detect plasma viremia from specimens that had previously been shown to be low or undetectable by commercial RNA load assays. The commercially available assays for quantitation of HIV-1 RNA in plasma were the AMPLICOR™ HIV-1 Monitor kit, which is based on PCR (Roche Molecular Systems, Raritan, N.J.); the Nuclisense™ HIV-1 QT assay (Organon Technika, Durham, N.C.) which is based on an isothermal nucleic acid sequence-based amplification (OTC); and the Quantiplex™ HIV RNA assay, which uses the branched DNA (bDNA) signal amplification techniques (Chiron Corp., Emoryville, Calif.) (Cavert, *AIDS* 12 (Suppl. A):S27 (1998)). These included 21 specimens, representing group M subtypes A-G, and group O, in which at least one of the three commercial assays were unable to detect the virus. Data is shown below in Table 4.

Subtype was ascribed based on a phylogenetic analysis of the env region. In some cases, the protease region was also sequenced to identify potential dual infections or recombinants. Specimen numbers 301-14, 301-27, 301-39, and 301-47 represented dual infections with multiple subtypes or potential recombinants of two different genotypes. The abbreviation "BLD" in Table 4 means that the samples were below detection. The abbreviation "ND" indicates that the assay was not done for that sample. The detection limit of each assay was 500 copies/ml for Chiron and 400 copies/ml for OTC and Roche.

TABLE 4

Comparative analysis of viral RNA detection in plasma using gp41 amplification assay vs. commercial viral load assays

| Specimen | Country | Subtype env/prt | Viral load assays | | | gp41 assay |
|---|---|---|---|---|---|---|
| | | | Chiron | OTC | Roche | |
| 301-06 | Ghana | A | $4 \times 10^3$ | $5 \times 10^3$ | BLD | + |
| 301-07 | Ghana | A | $5 \times 10^3$ | $2 \times 10^3$ | BLD | + |
| 301-12 | Ghana | A | $6 \times 10^4$ | $3 \times 10^4$ | BLD | + |
| 301-21 | Uganda | A/A | $7 \times 10^2$ | BLD | BLD | + |
| 301-24 | Uganda | A | BLD | $9 \times 10^2$ | $6 \times 10^2$ | + |

TABLE 4-continued

Comparative analysis of viral RNA detection in plasma using gp41 amplification assay vs. commercial viral load assays

| | | Subtype | Viral load assays | | | gp41 assay |
|---|---|---|---|---|---|---|
| Specimen | Country | env/prt | Chiron | OTC | Roche | + |
| 301-27 | Uganda | A/BD | BLD | BLD | BLD | + |
| TIA175 | Ivory Coast | A | ND | BLD* | BLD* | + |
| 301-14 | South Africa | C/B | $4 \times 10^3$ | BLD | $7 \times 10^2$ | + |
| 301-16 | South Africa | C | $3 \times 10^3$ | $9 \times 10^2$ | BLD | + |
| 301-29 | Zimbabwe | C | $>8 \times 10^5$ | $1 \times 10^3$ | BLD | + |
| 301-44 | India | C | $4 \times 10^3$ | BLD | $3 \times 10^3$ | + |
| 301-23 | Uganda | D | BLD | BLD | BLD | + |
| 301-26 | Uganda | D/D | $2 \times 10^3$ | BLD | $5 \times 10^2$ | + |
| 301-39 | Zimbabwe | E/A | $4 \times 10^3$ | BLD | BLD | + |
| 301-40 | Thailand | L | $2 \times 10^3$ | BLD | BLD | + |
| 301-47 | Argentina | F/B | BLD | BLD | BLD | + |
| 301-03 | Ghana | G | $1 \times 10^3$ | BLD | BLD | + |
| 301-08 | Ghana | G | $1 \times 10^3$ | $7 \times 10^2$ | BLD | + |
| DAA3671 | Ivory Coast | G | ND | BLD* | BLD* | + |
| DAA3760 | Ivory Coast | G | ND | BLD* | BLD* | + |
| 301-01 | Cameroon | O | BLD | BLD | BLD | + |

*Represents specimens which were still negative by ultrasensitive version of OTC and Roche (both with lower limit of detection of 50 copies/ml).

In addition, three specimens which were negative even by the ultrasensitive Roche and OTC assays were positive using the gp41 assay. Thus, all 21 (100%) of the 21 specimens, including one group O specimen, demonstrated a positive amplifiable signal by the consensus gp41 amplification assay. Taken together, the data demonstrate that the primers of the gp41 amplification assay provide better sensitivities for plasma viral RNA detection for all known subtypes of HIV-1 group M and group O viruses than currently available commercial assays.

EXAMPLE 6

Enhanced Sensitivity and Specificity with Detection of gp41 and Integrase Proteins Blood plasma samples obtained from HIV-positive patients were tested using the gp41 HIV-1 primers described herein (SEQ ID NOS: 1-9) to amplify and detect HIV-1 nucleic acids as described above. In addition, plasma samples were also obtained from 41 HIV-1-seronegative U.S. blood donors and 16 HIV-2-positive West Africans. Plasma samples from two captive chimpanzees (Noah and Niko) infected with SIVcpzANT were also tested as well as uncultured spleen and plasma from another captive chimpanzee (Marilyn) infected with SIVcpzUS.

Primers and Probes

Nested sets of PCR primers were designed based on highly conserved HIV-1 and SIVcpz regions in integrase and gp41. The outer primers of gp41 are the same as described in Examples 1-5 above and correspond to SEQ ID NOS: 1-3, and 5. The outer primers for integrase are INTFI (forward; SEQ ID NO. 6), and INTR1 (reverse; SEQ ID NO. 7); the inner primers are INTF2 (forward; SEQ ID NO.8) and INTR2 (reverse; SEQ ID NO.9). The protocols for RNA extraction and conditions for RT-PCR and PCR are as described above, except that an annealing temperature of 55° C. was used for the nested PCR with the integrase primer set.

Results

Figure 1:
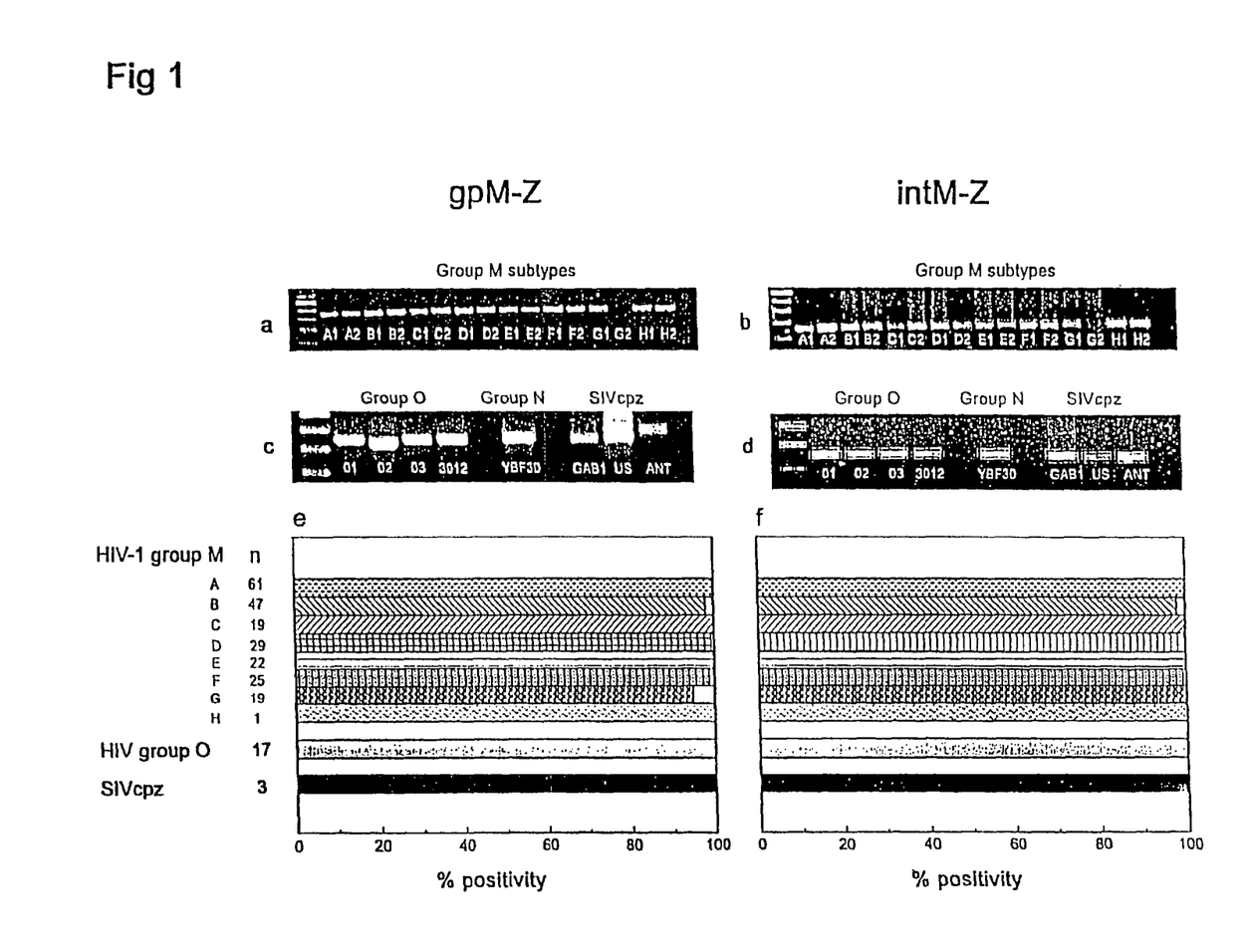
FIG. 1 shows the detection of diverse strains of HIV-1 group M, N and O and STVcpz using gp41 and integrase primer sets. Known copy numbers (10 and 5 copies per PCR reaction, abbreviated as A10 and A5, etc. for each subtype) of reference clones for HIV-1 group M subtype A (92UG037.1), B (YU2), C (92BR025.8), D (94UG 114.1), A/E (90CF402.8), F(93BR020.1), A/G (92NG003.1), and H (90CF056.1) amplified by gp41 (Panel A) and integrase (Panel C) are shown. Amplification of viral RNA and/or DNA representing HIV-1 group O (BCF01, 02, 03, and 3012), group N (YBF30), and SIVcpz (GAB1, US, and ANT) by primer pairs gp41 (Panel B) and integrase (Panel D) are also depicted.

Both gp41 and integrase primer sets reliably amplified as few as 10 copies of near full length clones of HIV-1 group M subtypes A-H. In most instances, 1 to 5 copies per PCR reaction were also detectable (FIG. 1, panels A and C, Table 5). Similarly, gp41 and integrase primer pairs amplified viral RNAs from culture supernatants of HIV-1 group O isolates (BCF1, BCF2, BCF3, and 3012), as well as cultured PBMC DNA from HIV-1 group N (YBF30) (FIG. 1, panels B and D, Table 5). Most importantly, both primer pairs amplified simian immunodeficiency viruses derived from two chimpanzee subspecies, i.e., SIVcpzGAB1, SIVcpzUS) and SIVcpzANT (FIGS. 1B and D, Table 5). However, none of the 4 SIVsm isolates were amplified with either primer set (Table 5). Thus, in contrast to the gp41 primer set described above, for groups M and O, i.e., SEQ. ID NOS.: 1-4, which does not amplify SIVcpz, the primer sets for gp41, i.e. SEQ ID NOS.: 1-3, 5 combined with those for integrase, SEQ. ID NOS.: 6-9 can amplify members of all known HIV-1 and SIVcpz lineages (Table 5).

Amplification of HIV-1 and SIVcpz Viral RNA from Plasma

Also examined was the amplification efficiency of gp41 and integrase primers in detecting plasma viremia from 216 HIV-1 group M (subtypes A-H) plasma specimens, and 17 HIV-1 group O specimens (Table 6). Of the 216 group M specimens, 214 (99%) were amplified by gp41 primers and 215 (99.5%) by integrase primers; one subtype B specimen was missed by both primers, whereas one subtype G was missed only by gp41 Cable 6). In addition, all 17 HIV-1 group O plasma specimens were amplified by both gp41 and integrase primers (Table 6). No plasma specimens from persons infected with group N viruses were available. Finally, both primer sets yielded positive amplifications from chimpanzee plasma samples. SIVcpzUS was amplified from the plasma of Marilyn and SIVcpzANT from the plasma of Noah and Niko (Table 6). By contrast, plasma specimens from the HIV-2-infected patients (n=16) and the HIV-1 negative blood donors (n=41) gave no amplifications (Table 6). Spiking of normal human plasma with known copy numbers of HIV-1 subtype B virus established that the gp41 primers can reliably detect as few as 25 copies/ml of HIV-1 RNA (data not shown).

Phylogenetic Classification

Figure 2A:
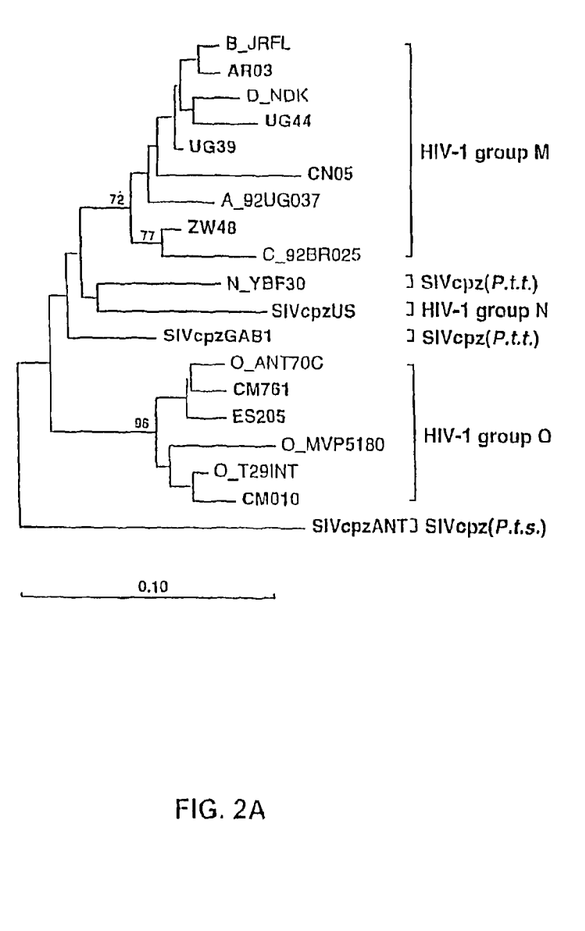
FIGS. 2A and 2B show the phylogenetic position of newly sequenced (in bold) and previously reported HIV-1 and SIVcpz strains in subgenomic pol (IN) (A) and env (gp41) (B) regions.
Figure 2B:
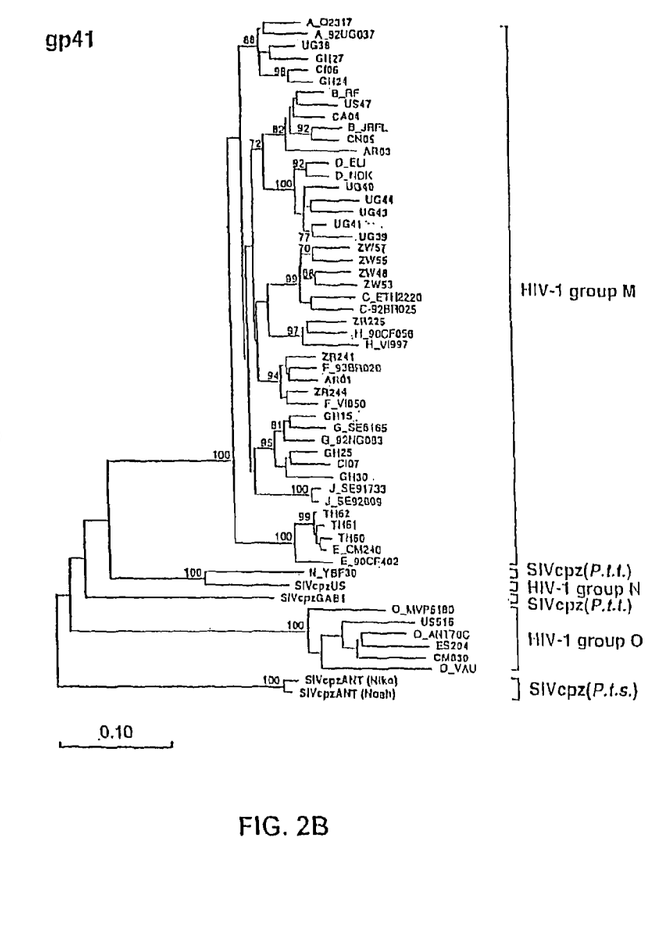

Phylogenetic analysis of primate lentiviral sequences provides the basis for their classification into groups and subtypes for HIV-1 and into major lineages for SIVcpz. An examination was made as to whether the sequences derived from the integrase and gp41 amplification products were of sufficient length to provide reliable phylogenetic information. Selected PCR products from 143 HIV-1 group M (A=22, B=34, C=19, D=24, E=22, F=9, G=12, and H=1), group O (n=17), and group N (YBF30) specimens and SIVcpz specimens (US, GAB 1, ANTnoah and ANTniko) were sequenced and used for phylogenetic tree construction. FIG. 2A depicts the relationships of sequences derived from the amplified integrase region. The topology shows an overall branching order very similar to the orders previously reported for full-length pol sequences. Newly amplified group M and O viruses (shown in bold) are readily identified as such, since they cluster with previously characterized reference sequences. YBF30, the single representative of HIV-1 group N, clusters as expected between groups M and O. Finally, the relative positions of the PCR-derived SIVcpzUS, SIVcpz-GAB 1, and SIVcpzANT integrase fragments are consistent with those previously identified for their full length sequences. The only shortcoming of the amplified IN region is that it is not suitable (because of its length and conservation) for more detailed subtype classification of HIV-1 group M viruses. However, such classification is possible for sequences derived from the gp41 amplification products. As shown in FIGS. 2A and B, a phylogenetic tree constructed from the subgenomic gp41 sequences yields an overall topology that is very similar to that of a full length env tree. Thus, 28 newly sequenced group M viruses (depicted in bold) are readily classified into group M subtypes A (4), B(4), C (4), D (5), E (3), F (3), G (4), and H (1). Finally, analysis of gp41 sequences can also be used to classify new SIVcpz strains. Sequences amplified from the plasma of a chimpanzee (Niko) experimentally infected with SIVcpzANT cluster very closely with sequences derived from the plasma of the chimpanzee (Noah) naturally infected with this isolate. Taken together, a PCR-based approach that utilizes both integrase and gp41 primers should be useful in assays to definitively type newly identified HIV-1 as well as SIVcpz strains.

TABLE 5

Cross-reactivity of gp41 and integrase primer sets

| HIV/SIV | NAME | MATERIAL | gp41 region gpM/O* | gp41 region gpM-Z | Integrase |
|---|---|---|---|---|---|
| HIV-1 Group M | | | | | |
| Subtype A | 92UG027.1 | clone | 1 | 1 | 1 |
| Subtype B | YU2 | clone | 5 | 5 | 1 |
| | SG3 | clone | 1 | 1 | 1 |
| Subtype C | 92BR025.8 | clone | 1 | 1 | 1 |
| Subtype D | 94UG114.1 | clone | 1 | 1 | 1 |
| Subtype A/E | 90CF402.8 | clone | 5 | 5 | 5 |
| Subtype F | 93BR020.1 | clone | 5 | 5 | 1 |
| Subtype A/G | 92NG003.1 | clone | 1 | 1 | 10 |
| Subtype H | 90CF056.1 | clone | 1 | 1 | 1 |
| Group O | BCF01 | culture sup | + | + | + |
| | BCF02 | culture sup | + | + | + |
| | BCF03 | culture sup | + | + | + |
| | 3012 | culture sup | + | + | + |
| Group N | YBF30 | Cultured PBMC DNA | + | + | + |
| SIVcpz | SIVcpzUS | spleen | + | + | + |
| | SIVspzBAB1 | cultured sup | − | + | + |
| | SIVcpzANT | cultured PBL | − | + | + |
| SIVsm | SIVsm3 | cultured PBL | − | − | − |
| | SIVsm21 | cultured PBL | − | − | − |
| | SIVsm55 | cultured PBL | − | − | − |
| | SIVsm156 | cultured PBL | − | − | − |

*The amplification using the primer sets is shown as number of copies per PCR reaction amplified for HIV-1 group M reference clones, and as positive (+) or negative (−) amplification for HIV-1 group O and group N, and SIV isolates.

TABLE 6

Amplification of HIV-1 (groups M and O) and SIV cpz viral RNA in human and chimpanzee plasmas using gp41 and integrase primer sets

| HIV Type | Country of origin | #.tested | RT-PCR amplification of plasma gp41 | RT-PCR amplification of plasma integrase |
|---|---|---|---|---|
| HIV-1 Group M Subtype A | | | | |
| | Ghana | 11 | 11 | 11 |
| | Ivory Coast | 25 | 25 | 25 |
| | Uganda | 21 | 21 | 21 |
| | Misc | 4 | 4 | 4 |
| Total | | 61 | 61 | 61 |
| Subtype B | | | | |
| | Brazil | 17 | 16 | 16 |
| | Thailand | 17 | 17 | 17 |
| | Misc | 13 | 13 | 13 |
| Total | | 47 | 46 | 46 |
| Subtype C | | | | |
| | Uganda | 4 | 4 | 4 |
| | Zimbabwe | 8 | 8 | 8 |
| | Mozambique | 5 | 5 | 5 |
| | India | 2 | 2 | 2 |
| Total | | 19 | 19 | 19 |
| Subtype D | | | | |
| | Uganda | 28 | 28 | 28 |
| | Lebanon | 1 | 1 | 1 |
| Total | | 29 | 29 | 29 |
| Subtype L | | | | |
| | Thailand | 22 | 22 | 22 |
| Subtype F | | | | |
| | Argentina | 23 | 23 | 23 |
| | Japan | 2 | 2 | 2 |
| Total | | 25 | 25 | 25 |
| Subtype G | | | | |
| | Ivory Coast | 9 | 8 | 9 |
| | Ghana | 3 | 3 | 3 |
| Total | | 12 | 11 | 12 |
| Subtype H | | | | |
| | Zaire | 1 | 1 | 1 |
| HIV-1 Group O | | | | |
| | Cameroon | 8 | 8 | 8 |
| | Spain | 7 | 7 | 7 |
| | US | 2 | 2 | 2 |
| Total | | 17 | 17 | 17 |
| SIVcpz | | | | |
| | SIVcpzUS (Marilyn) | 1 | 1 | 1 |
| | SIVcpzANT (Noah) | 1 | 1 | 1 |
| | SIVcpzANT (Niko) | 1 | 1 | 1 |
| Total | | 3 | 3 | 3 |
| HIV-2 | | 16 | 0 | 0 |
| HIV negative | | 41 | 0 | 0 |

The disclosures of all publications cited in this application are hereby incorporated by reference in their entireties in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

What is claimed is:

1. A nucleic acid primer comprising an oligonucleotide having a length of 18-40 nucleotides, wherein the oligonucleotide selectively hybridizes to a region of an HIV nucleic acid molecule, the region selected from between the nucleotide positions 7746 to 7772; 7817 to 7844; 8220 to 8258; 8347 to 8374; 8432 to 8459; 7850 to 7879; 8265 to 8294; or 8281 to 8310 of the HXB2 strain.

2. The primer of claim 1, wherein the oligonucleotide comprises a nucleic acid sequence selected from the group consisting of SEQ ID NO: 2, SEQ ID NO: 3, SEQ ID NO: 4, and SEQ ID NO: 5.

3. A method of detecting a virus selected from a HIV-1 group M, a HIV-1 group N, a HIV-1 group O or a SIVcpz in a biological sample in vitro comprising
combining the sample with a first primer under selective hybridization conditions for the selective hybridization of the first primer to nucleic acids in the sample, wherein the first primer comprises the nucleic acid primer of claim 1; and
assaying hybridization of the primer to the nucleic acids in the sample,
wherein detection of hybridization of the primer to the nucleic acids indicates the presence of the HIV-1 group M, the HIV-1 group N, the HIV-1 group O or the SIVcpz in the sample.

4. The method of claim 3, wherein the oligonucleotide comprises a nucleic acid sequence selected from the group consisting of SEQ ID NO: 2, SEQ ID NO: 3, SEQ ID NO: 4, and SEQ ID NO: 5.

5. The method of claim 3, further comprising combining the sample comprising the first primer with a second primer under selective hybridization conditions for the selective hybridization of the second primer to nucleic acids in the sample, wherein the second primer comprises an oligonucleotide that selectively hybridizes to a second highly conserved region of the nucleic acid molecule of HIV-1 , wherein the oligonucleotide that selectively hybridizes to the second highly conserved region of the nucleic acid molecule of HIV-1 (i) selectively hybridizes to the region between nucleotide positions selected from the group consisting of 7746 to 7772; 7817 to 7844; 8220 to 8258; 8347 to 8374; 8432 to 8459; 7850 to 7879; 8265 to 8294; and 8281 to 8310 of the HXB2 strain, or (ii) consists of the nucleic acid sequence set forth as SEQ ID NO: 1,
wherein the first primer and the second primer are a first primer pair, and wherein the primer pair and the sample are incubated under nucleic acid amplification conditions to amplify HIV-1 nucleic acids in the sample.

6. The method of claim 5, wherein the second primer has a nucleic acid sequence selected from the group consisting of SEQ ID NO: 2, SEQ ID NO: 3, SEQ ID NO: 4, and SEQ ID NO: 5.

7. The method of claim 5, wherein the first primer of the first primer pair is a reverse primer comprising SEQ ID NO: 2 and the second primer of the first primer pair is a forward primer consisting of SEQ ID NO: 1.

8. The method of claim 5, further comprising a second primer pair, wherein the first and the second primer pairs are nested.

9. The method of claim 8 wherein the first primer of the second primer pair is a forward primer comprising SEQ ID NO: 3 and the second primer of the second primer pair is a reverse primer comprising a nucleotide sequence selected from the group consisting of SEQ ID NO: 4 and SEQ ID NO: 5.

10. The method of claim 5, wherein the amplification conditions comprise 3-40 cycles of heating at 93-97° C. for 30-90 seconds, at 45-57° C. 30-90 seconds, and 70-94° C. for 30-90 seconds.

11. A nucleic acid primer comprising an oligonucleotide having a length of 18-40 nucleotides, wherein the oligonucleotide selectively hybridizes to a region of an HIV nucleic acid molecule, the region selected from between nucleotide positions 4550 to 4625; 4626 to 4753; 4596 to 4625; 4724 to 4753; and 5051 to 5080 of the HXB2 strain.

12. The primer of claim 11, wherein the oligonucleotide has a nucleic acid sequence selected from the group consisting of SEQ ID NO: 6, SEQ ID NO: 7, and SEQ ID NO: 8.

13. A method for detecting an HIV-1 group N or a chimpanzee SIV in a biological sample in vitro comprising:
  combining the biological sample with a first primer under selective hybridization conditions for the selective hybridization of the first primer to nucleic acids in the sample, wherein the first primer comprises the primer of claim 12, and
  assaying hybridization of the primer to the nucleic acids, wherein detection of hybridization of the primer to the nucleic acids indicates the presence of the HIV-1 group N or the chimpanzee SIV in the biological sample.

14. The method of claim 13, further comprising combining the sample comprising the first primer with a second primer that hybridizes to a second highly conserved region of the nucleic acid molecule between nucleotide positions 4450 and 5126 of the HXB2 strain of HIV-1, wherein the oligonucleotide does not selectively hybridize to a region of the HXB2 strain between nucleotide positions 4754-4984, wherein the first and second primers are a primer pair, and wherein the primer pair and the sample are incubated under nucleic acid amplification conditions to amplify HIV-1 nucleic acids in the sample.

15. The method of claim 14, wherein the first primer comprises SEQ ID NO: 6 or SEQ ID NO: 8 and the second primer comprises SEQ ID NO: 7.

16. A method of detecting a virus selected from a HIV-1 group M, a HIV-1 group N, a HIV-1 group O or a SIVcpz in a biological sample in vitro comprising:
  combining the sample with a first primer under selective hybridization conditions for the selective hybridization of the first primer to nucleic acids in the sample, wherein the first primer comprises the nucleic acid primer of claim 11; and
  assaying hybridization of the primer to the nucleic acids, wherein detection of hybridization of the primer to the nucleic acids indicates the presence of the HIV-1 group M, the HIV-1 group N, the HIV-1 group O or the SIVcpz in the sample.

17. The method of claim 16, wherein the oligonucleotide has a nucleic acid sequence selected from the group consisting of SEQ ID NO: 6, SEQ ID NO: 7, and SEQ ID NO: 8.

18. The method of claim 17, further comprising the step of combining the sample with a second primer under selective hybridization conditions for the selective hybridization of the second primer to nucleic acids in the sample, wherein the second primer comprises an oligonucleotide that selectively hybridizes to a second highly conserved region of the nucleic acid molecule of HIV-1 between nucleotide positions selected from the group consisting of 4550 to 4625; 4626 to 4753; and 5051 to 5080 of the HXB2 strain, wherein the first primer and the second primer are a first primer pair, and wherein the primer pair and the sample are incubated under nucleic acid amplification conditions to amplify HIV-1 nucleic acids in the sample.

19. The method of claim 18, wherein the second primer has a nucleic acid sequence selected from the group consisting of SEQ ID NO: 6, SEQ ID NO: 7, and SEQ ID NO: 8.

20. The method of claim 18, wherein the first primer of the first primer pair is a forward primer comprising SEQ ID NO: 6 and the second primer of the first primer pair is a reverse primer comprising SEQ ID NO: 7.

21. The method of claim 20, further comprising a second primer pair, wherein the first and second primer pairs are nested, wherein the first primer of the second primer pair is a forward primer comprising SEQ ID NO: 8.

22. A nucleic acid primer consisting of SEQ ID NO: 1.

23. A method for detecting HIV-1 group N or chimpanzee SIV in a biological sample comprising:
  combining the sample with a first primer under selective hybridization conditions for the selective hybridization of the first primer to nucleic acids in the sample, wherein the first primer comprises the nucleotide sequence of SEQ ID NO: 5, and
  assaying hybridization of the primer to the nucleic acids, wherein detection of hybridization of the primer to the nucleic acids indicates the presence of the HIV-1 group N or the chimpanzee SIV in the sample.

24. The method of claim 23 further comprising combining the sample comprising the first primer with a second primer that hybridizes to a highly conserved region of a nucleic acid molecule between nucleotide positions 7789 to 7816; 7746 to 7772; 7817 to 7844; 8220 to 8258; or 7850 to 7879; of the HXB2 strain of HIV-1 , wherein the first primer and the second primer are a primer pair, and wherein the primer pair and the sample are incubated under nucleic acid amplification conditions to amplify HIV-1 nucleic acids in the sample.

25. The method of claim 24, wherein the first primer comprises SEQ ID NO: 5 and the second primer consists of SEQ ID NO: 1 or comprises SEQ ID NO: 3.

* * * * *

SEQUENCE LISTING

<160> NUMBER OF SEQ ID NOS: 9

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: primer for
      HIV-1

<400> SEQUENCE: 1
tcttaggagc agcaggaagc actatggg                                          28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: reverse
      primer for HIV-1

<400> SEQUENCE: 2
aacgacaaag gtgagtatcc ctgcctaa                                          28

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: primer for
      HIV-1

<400> SEQUENCE: 3
acaattattg tctggtatag tgcaacagca                                        30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: reverse
      primer for HIV-1

<400> SEQUENCE: 4
ttaaacctat caagcctcct actatcatta                                        30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: alternate
      reverse primer for HIV-1

<400> SEQUENCE: 5
tcctactatc ttaatgaata tttttatata                                        30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: primer for
      HIV-1

```
<400> SEQUENCE: 6
agtgctgcag ttaaggcagc ctgttggtgg                                    30

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: reverse
      primer for HIV-1

<400> SEQUENCE: 7
ctacctgcca gacaatcatc acctgccatc                                    30

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: primer
      for HIV-1

<400> SEQUENCE: 8
aagagatcaa gctgaacatc ttaagacagc                                    30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:  reverse
      primer for HIV-1

<400> SEQUENCE: 9
tgtattacta ctgccccttc acctttcca                                     29
```